(12) United States Patent
Double et al.

(10) Patent No.: US 6,172,263 B1
(45) Date of Patent: Jan. 9, 2001

(54) TAMOXIFEN AND ANALOGUES THEREOF

(75) Inventors: John Double; Derek Maitland, both of Bradford (GB); Ioana Popa, Chapel Hill, NC (US)

(73) Assignee: Bradford University, West Yorkshire (GB)

( * ) Notice: Under 35 U.S.C. 154(b), the term of this patent shall be extended for 0 days.

(21) Appl. No.: 09/118,836

(22) Filed: Jul. 20, 1998

Related U.S. Application Data

(63) Continuation-in-part of application No. PCT/GB97/00134, filed on Jan. 20, 1997.

(30) Foreign Application Priority Data

Jan. 20, 1996 (GB) .................................................. 9601167
Sep. 9, 1996 (GB) .................................................. 9618775

(51) Int. Cl.[7] .............................................. C07C 213/00
(52) U.S. Cl. ........................................ 564/317; 564/319
(58) Field of Search ..................................... 564/317, 319

(56) References Cited

FOREIGN PATENT DOCUMENTS

| 0 127 128 | 12/1984 | (EP) . |
|---|---|---|
| 0 168175 | 1/1986 | (EP) . |
| 0 313 799 | 9/1988 | (EP) . |
| 0 287 690 | 10/1988 | (EP) . |
| 1064629 | 4/1967 | (GB) . |
| 2 309 224 | 7/1997 | (GB) . |
| 95/11879 * | 5/1995 | (WO) . |
| 95/18786 | 7/1995 | (WO) . |

OTHER PUBLICATIONS

McCague, R. et al J. Chem. Soc. Perkin Trans 2 (1988) (7) 1201–8.*
Journal of the Chemical Soc. Perkin Transactions 1987, Letchworth, pp. 1011–1015.
Srikanth, Natarajan et al., "Synthesis of heterocyclic analogs of tamoxifen as potential antiestrogens" J Chem Res., SYNOP. (1997)(8) 274–275, XP002087119, see page 274.
M Jarman et al "The use of Octafluorotoluene and pentafluoropyridine in the Synthesis of Pure Z–and–E isomer of derivatives of tamoxifen". J. Chem Res Synop. (1985), (4), 116–117.

* cited by examiner

Primary Examiner—Paul J. Killos
(74) Attorney, Agent, or Firm—Arent Fox Kintner Plotkin & Kahn, PLC

(57) ABSTRACT

A method of preparing a first geometric isomer of tamoxifen or an analogue comprises allowing the first isomer to crystallize in hexanol and the product thereof to crystallize in methanol and then derivatising the product of the methanol crystallization to prepare said first isomer in very high purity.

22 Claims, 8 Drawing Sheets

TAMOXIFEN AND ANALOGUES THEREOF

CROSS REFERENCE TO RELATED APPICATION

This application is a continuation-in-part of International Application PCT/GB97/00134, filed Jan. 20, 1997, and designating the U.S.

This invention relates to tamoxifen and analogues thereof and particularly, although not exclusively, relates to a method of preparing a desired isomer of tamoxifen or an analogue thereof.

Tamoxifen is a triphenylethylene derivative of formula

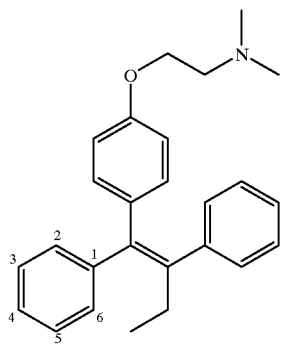

which is a drug in clinical use for the treatment of hormone dependent breast cancer. For this purpose, only the Z isomer has the required antiestrogenic activity, the E isomer being oestrogenic. The same criteria of antioestrogenecity applies to tamoxifen analogues. One of the most important analogues of tamoxifen is 4-hydroxytamoxifen (one of the main metabolites in patients), which has an affinity for binding to oestrogen receptors which is 100 times higher than for tamoxifen itself. Accordingly, processes for stereoselective synthesis and/or isolation of substantially pure Z isomer of tamoxifen, 4-hydroxytamoxifen and other analogues are desirable.

Known processes for the preparation of substantially pure Z isomer of tamoxifen and 4-hydroxytamoxifen include stereoselective syntheses (involving expensive catalysts) as described in J. Chem. Soc., Perkin Trans I 1987, 1101 and J. Org. Chem. 1990, 55, 6184 or chromatographic separation of an E/Z mixture of isomers as described in J. Chem. Res., 1985 (S) 116, (M) 1342, 1986 (S) 58, (M) 771.

It is an object of the present invention to provide a method of preparing tamoxifen or an analogue thereof which is rich in the desired isomer and which may be advantageous over known methods.

The invention is based on the surprising, and previously unappreciated, discovery that one geometric isomer of tamoxifen or an analogue thereof can be predominantly removed from a mixture of isomers in the presence of certain solvents.

According to a first aspect of the invention, there is provided a method of removing predominantly a first geometric isomer of tamoxifen or an analogue thereof from a mixture comprising said first geometric isomer and a second geometric isomer, the method including the step of allowing the first isomer to crystallise in a solvent.

Preferably, the method comprises contacting a mixture which comprises said first and second isomers with said solvent.

The method may include separating the crystallised product from the remainder.

Said solvent is preferably able to dissolve the isomers in said mixture and is such as to allow re-crystallisation as aforesaid. In the method, said solvent is preferably contacted with the isomers in the mixture when said solvent is at a first temperature wherein said first temperature is suitably less than the boiling point of the solvent. Recrystallisation is suitably carried out at a second temperature which is less than said first temperature. It is believed that the temperature of the recrystallisation step affects the relative amounts of first and second isomers in the recrystallised product. For example, it has been observed that, if recrystallisation is carried out in a freezer at −4° C., then the ratio of the amount of the second geometric isomer to the first geometric isomer in the crystallised product is greater than the corresponding ratio observed when recrystallisation is carried out at ambient temperature (about 22° C.). Thus, recrystallisation is suitably carried out at greater than −4° C., preferably greater than 0° C., more preferably greater than 10° C., especially greater than 20° C. Advantageously, recrystallisation may be carried out at at least ambient temperature.

It will be appreciated that there may be an optimum temperature of recrystallisation wherein the ratio of the amount of first geometric isomer to second geometric isomer in the crystallised product is maximised. Said second temperature may be within 30° C., suitably 25° C., preferably 20° C., more preferably 15° C., especially 10° C. of the optimum temperature.

Said first temperature may be at least 50° C., suitably at least 60° C., preferably at least 70° C., more preferably at least 80° C., especially at least 90° C. Said first temperature may be less than 200° C., preferably less than 160° C., more preferably less than 140° C., especially less than 120° C.

Said first temperature may be less than the boiling point of the solvent, suitably by at least 10° C., preferably at least 20° C., more preferably at least 30° C., especially at least 40° C.

Said solvent may have a boiling point of at least 30° C., suitably at least 40° C., preferably at least 50° C., more preferably at least 60° C. Said boiling point may be less than 300° C., suitably less than 250° C., preferably less than 200° C., more preferably less than 175° C.

Various solvents may be selected for use in the method. Preferably, said solvent includes a first solvent part. Preferably, the first solvent part is an organic solvent with polar organic solvents being preferred.

Said first solvent part may be an unsubstituted hydrocarbon or may include one or more functional groups. Such groups may be selected from —OH, —NO$_2$, —CN, —O— and optionally substituted, especially unsubstituted, alkyl groups.

The first solvent part may include two or, more preferably, one or fewer functional groups. Especially preferred is the case wherein the first solvent part includes only one functional group.

Said first solvent part is preferably a protic solvent.

A preferred functional group of said first solvent part is an —OH group.

Said first solvent part may be aliphatic, alicyclic, aromatic or heteroaromatic. Said first solvent part is preferably aliphatic.

Said first solvent part may include one or more, suitably at least two, preferably at least three, more preferably at least four, especially at least five carbon atoms. Said first solvent part may include twelve or fewer, suitably ten or fewer, preferably nine or fewer, more preferably eight or fewer, especially seven or fewer, carbon atoms.

Said first solvent part may have a boiling point of at least 50° C., suitably at least 75° C., preferably at least 100° C., more preferably at least 125° C., especially at least 150° C. Said boiling point may be less than 300° C., suitably less than 25° C., preferably less than 225° C., more preferably less than 200° C., especially less than 175° C.

Said first solvent part is preferably an alcohol having one —OH group. Said first solvent part is more preferably hexanol.

Said solvent may include a mixture comprising said first solvent part and a second solvent part. Said second solvent part may include any feature of said first solvent part described herein. Preferably, however, said solvent consists essentially of said first solvent part as described.

The method preferably includes a first step comprising allowing the first isomer to crystallise in a solvent as aforesaid and a second step which comprises allowing the product of the first step to crystallise in a solvent.

The solvent used in the second step (hereinafter "said second solvent") may have any feature of the solvent used in the first step (hereinafter "said first solvent"). Preferably, said first solvent and said second solvent are different. Preferably, said second solvent has a lower boiling point than said first solvent, suitably by at least 30° C., preferably at least 50° C., more preferably at least 70° C., especially at least 85° C.

The boiling point of the second solvent may be less than 95° C., is suitably less than 80° C., is preferably less than 70° C. and is, more preferably, less than about 65° C.

Said second solvent is preferably an alcohol, preferably a $C_{1-4}$ alcohol, especially a $C_{1-2}$ alcohol, with methanol being most preferred.

Preferably, the mixture used in the first step of the method is substantially pure. Thus, prior to said first step, there may be a purifying step. This may simply comprise washing a mixture to be used in said first step with a solvent. The solvent used in the washing (hereinafter "said third solvent") may have any feature of said second solvent as described. Preferably, the temperature of the third solvent in said washing step is less than the temperature of said first solvent when it is used and/or the temperature of said second solvent when it is used. Said third solvent preferably is the same as said second solvent and is, therefore, preferably methanol.

Preferably, said first geometric isomer is crystallised at some stage of said method from a solvent which includes or, preferably consists essentially of methanol.

By "consists essentially", we mean that a solvent comprises at least 80 wt %, preferably at least 90 wt %, more preferably at least 95 wt %, especially at least 99 wt % of the referenced solvent, for example methanol.

Said first step and/or said second step may be carried out under less than ambient light conditions. Preferably, said step(s) is/are carried out substantially in the dark. Preferably, the method uses a receptacle which is substantially opaque. Excluding or reducing the light intensity in said first and/or second steps is found to increase the amount of the preferred isomer isolated.

In the context of this specification, the term "analogue" includes: a derivative of tamoxifen wherein one or more atoms or groups of tamoxifen have been replaced by other atoms or groups; or wherein a ring or rings is/are formed between juxtaposed atoms or groups of tamoxifen; and a precursor of tamoxifen or a derivative thereof which precursor exists in at least two geometric isomeric forms and which can be converted to tamoxifen or a said derivative thereof, suitably by a substitution reaction.

Various analogues of tamoxifen which fall within the scope of the present invention are described in Endocrine Reviews, 11(4), 1990, 578–603.

Analogues of tamoxifen may include optionally-substituted triphenylalkyl or alkylene compounds. Preferred optionally-substituted triphenyl compounds are of general formula

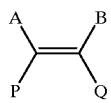

(I)

wherein A, B and P each independently represents an optionally-substituted phenyl group and Q represents a hydrogen atom or an optionally-substituted alkyl, alkenyl, alkynyl or phenyl group; and wherein a pair of adjacent substituents A, B, P and Q are optionally arranged together to form part of a ring structure.

It will be appreciated that the compound of general formula I may exist in different geometric isomeric forms and the formula is not intended, unless otherwise stated herein, to be limited to any such form.

Optional substituents as described herein include any substituents generally used to affect the activity of drugs for oral administration or which represent leaving groups and/or protecting groups which aid the preparation of such drugs. In relation to alkyl, alkenyl, alkynyl and phenyl groups, preferred optional substituents include halogen atoms, haloalkyl and hydroxy groups and optionally-substituted alkylcarboxy, alkoxy, phenoxy, alkylamino and alkylcarbonyl groups.

Preferred alkyl, alkenyl and alkynyl groups may have up to 12, preferably up to 6, more preferably up to 4 carbon atoms.

Preferably, Q represents an optionally-substituted, preferably unsubstituted, alkyl group. Preferably, said alkyl group is a $C_1$ to $C_4$, more preferably a $C_1$ to $C_2$, alkyl group. Q preferably represents an ethyl group.

Preferably, groups A, B and P independently represent an unsubstituted or monosubstituted phenyl group. Where a group A, B or P is substituted, it is preferably substituted in the 3- or, more preferably, the 4-position.

Preferably, group B is unsubstituted.

Group P is preferably unsubstituted or substituted by a halogen atom or hydroxy, optionally-substituted alkoxy or phenoxy, groups. Where group P is substituted, it is preferably substituted in the 4-position. More preferably, group P is unsubstituted or substituted by an optionally-substituted phenoxy group. In an especially preferred embodiment, P is unsubstituted. Thus, preferably P represents an unsubstituted phenyl group.

Preferably, group A is monosubstituted by a halogen atom or hydroxy, optionally-substituted alkoxy or phenoxy, groups. Preferably, group A is monosubstituted by an optionally-substituted alkoxy group. A preferred optionally-substituted alkoxy group is of general formula —O—(CH$_2$)$_n$—X  (II)

wherein n represents an integer preferably in the range 1 to 8, more preferably 1 to 4, especially 1 to 2; and X represents a leaving group, for example a halogen, especially a chlorine, atom, or a group of general formula

  (III)

wherein R$^1$ and R$^2$ independently represent a hydrogen atom or an optionally-substituted, preferably unsubstituted, alkyl group.

Preferably, n represents 2. In a preferred embodiment, group A is monosubstituted by an alkoxy group of general formula II, wherein n represents 2.

Preferably, said mixture used in the method comprises a first analogue of tamoxifen (preferably a precursor of tamoxifen or tamoxifen derivative as described above) and the method includes the further step of derivatising the first geometric isomer removed in order to prepare tamoxifen or a derivative, especially an antiestrogenic derivative, thereof. Preferably, the first analogue of tamoxifen, more preferably said first geometric isomer of said first analogue, has less antiestrogenic activity compared to tamoxifen or a said derivative which is prepared in said further derivatising step.

Preferably, said precursor is a compound of general formula I described above wherein B, P and Q are as described above. Preferably, A represents a phenyl group substituted, preferably at least at the 4-position, by a first moiety which includes an active atom or group which is arranged to react with a second moiety which includes a group of general formula III as described above in order to produce an optionally substituted alkoxy group of general formula II as described above. Preferably, said first moiety includes a leaving group which is suitably X as described above. Preferably, said first moiety comprises a group of general formula II as described above. Said first moiety is preferably reacted with an amine of general formula R$^1$R$^2$NH wherein R$^1$ and R$^2$ are as described above.

Where a pair of adjacent substituents A, B, P and Q are arranged together to form part of a ring structure, the ring structure may be formed between pairs of substituents A, B, P and Q which are cis to one another. Examples of compounds of general formula I which have ring structures as described include:

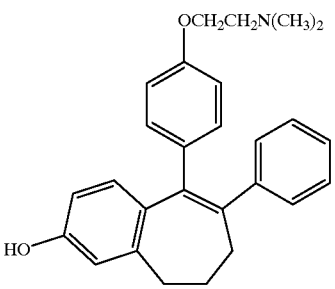  IV

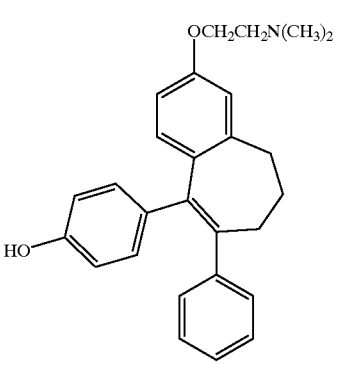  V

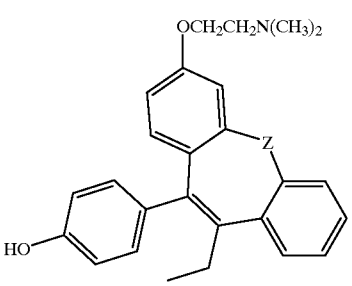  VI wherein Z represents an oxygen or sulphur atom or a group —CH$_2$CH$_2$—.

Preferably, adjacent substituents A, B, P and Q do not form part of a ring structure.

When the method involves contacting a mixture which comprises first and second isomers, the mixture used may be prepared by known routes to tamoxifen and its derivatives for example as described in J.Chem. Research, 1985(S) 116, (M) 1342 and 1986 (S) 58, (M) 0771.

A precursor of tamoxifen or tamoxifen derivative for use in the method may be prepared from a compound of general formula

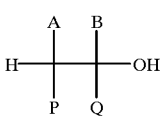  (XII)

wherein A, B, P and Q are as described in any statement herein. Preferably, A, B, P and Q in said compounds of formula I and XII represent the same atoms or groups.

Advantageously, the compound of formula XII may be dehydrated to prepare the compound of formula I. Dehydration may involve refluxing the compound of formula XII in a solvent in the presence of a strong acid, for example concentrated hydrochloric acid.

A typical reaction scheme for preparing tamoxifen is as shown below in Scheme I.

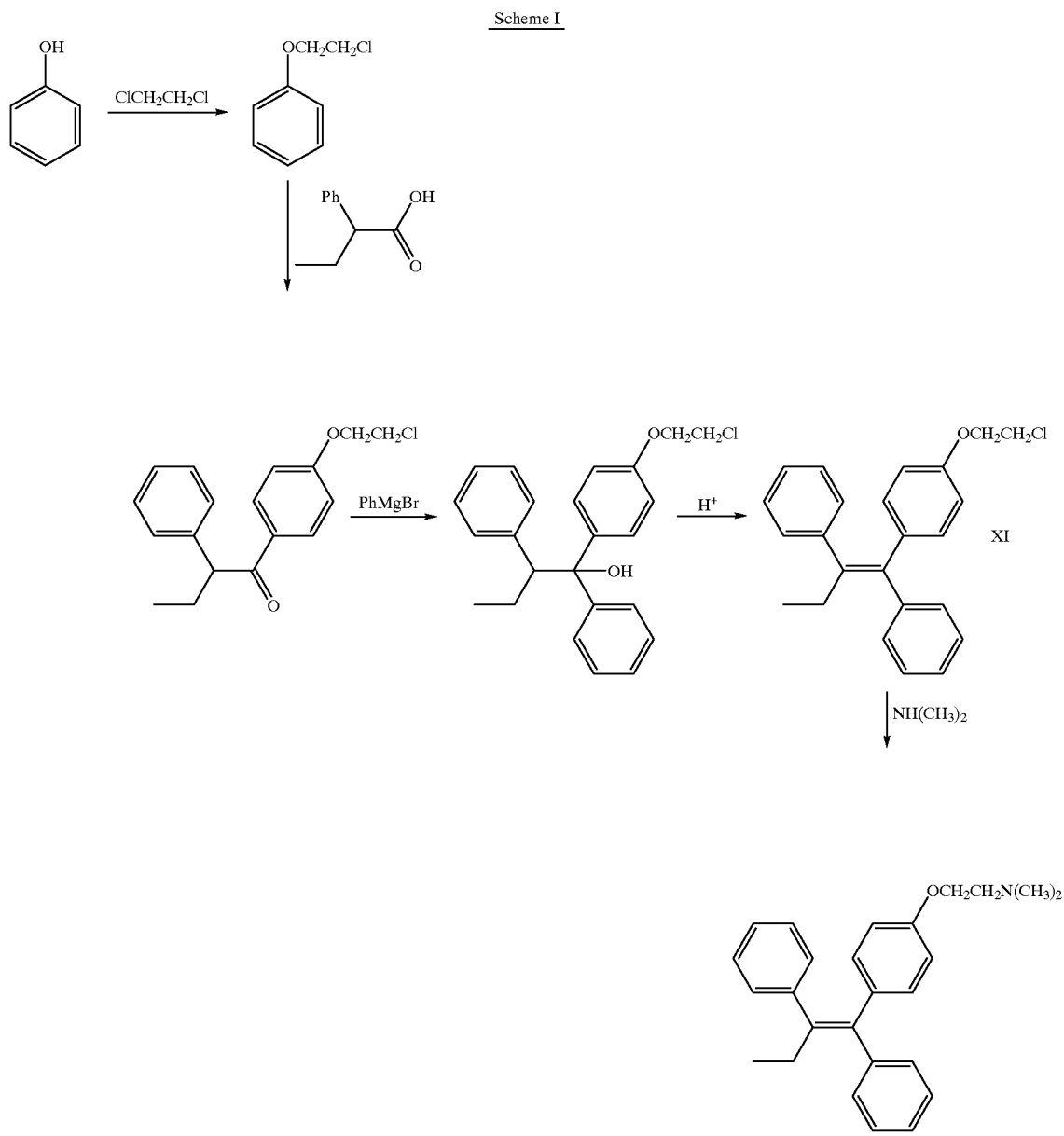

Scheme I

Referring to Scheme I, preferably, the alkene derivative of formula XI is contacted with said solvent prior to the reaction with dimethylamine. In one embodiment, it is found that, after washing a mixture of geometric isomers of said compound XI with methanol, followed by a first recrystallisation step using hexanol and a second recrystallisation step using methanol, the compound XI prepared contains 100% (according to HPLC analysis) of the desired Z isomer (which has the stereochemical configuration of compound XI shown in Scheme I). Compound XI can then be converted by a simple reaction to tamoxifen with the stereochemistry being maintained. Thus, in general terms, the method described above may be used to prepare tamoxifen or an analogue which includes greater than 99 wt %, suitably greater than 99.5 wt %, preferably greater than 99.7 wt %, more preferably greater than 99.8 wt %, especially greater than 99.9 wt %, of said first geometric isomer.

A typical process for preparing 4-hydroxytamoxifen involves derivatising compound X prepared according to the reaction scheme provided below.

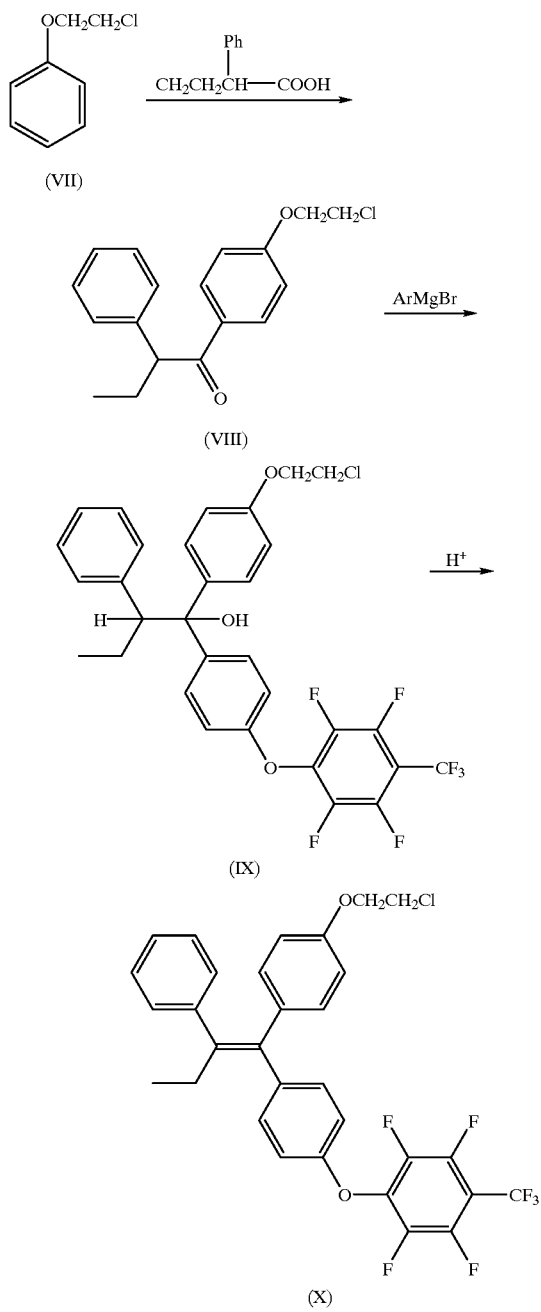

(VII)

(VIII)

(IX)

(X)

The invention extends to pharmaceutically acceptable forms, for example salts of tamoxifen or analogues thereof.

The invention extends to a method of preparing tamoxifen or a derivative, especially an antiestrogenic derivative, thereof, the method including the steps of allowing a first geometric isomer of a precursor of tamoxifen or said derivative to crystallise in a solvent and derivatising said precursor in order to produce said tamoxifen or said derivative.

The invention extends to the use of a solvent for removing predominantly a first geometric isomer of tamoxifen or an analogue thereof from a mixture of isomers.

The invention extends to a method of preparing an antiestrogenic isomer of tamoxifen or an analogue thereof in purity of at least 99%, suitably at least 99.5%, preferably at least 99.7%, more preferably at least 99.8%, especially at least 99.9%, most preferably at least 99.95%, the method using a solvent as described herein.

The invention extends to the product of any process described herein.

Any feature of any aspect or embodiment described herein may be combined with any feature of any other aspect or embodiment described herein.

The invention will now be described, by way of example, with reference to the accompanying figures wherein:

FIG. 1 is a $^1$H NMR spectrum for a mixture of isomers of a tamoxifen precursor, prepared in Example 1;

FIGS. 2 to 4 provide further detail for the spectrum of FIG. 1;

EXAMPLE 1

Preparation of Z isomer of Tamoxifen

Figure 7:
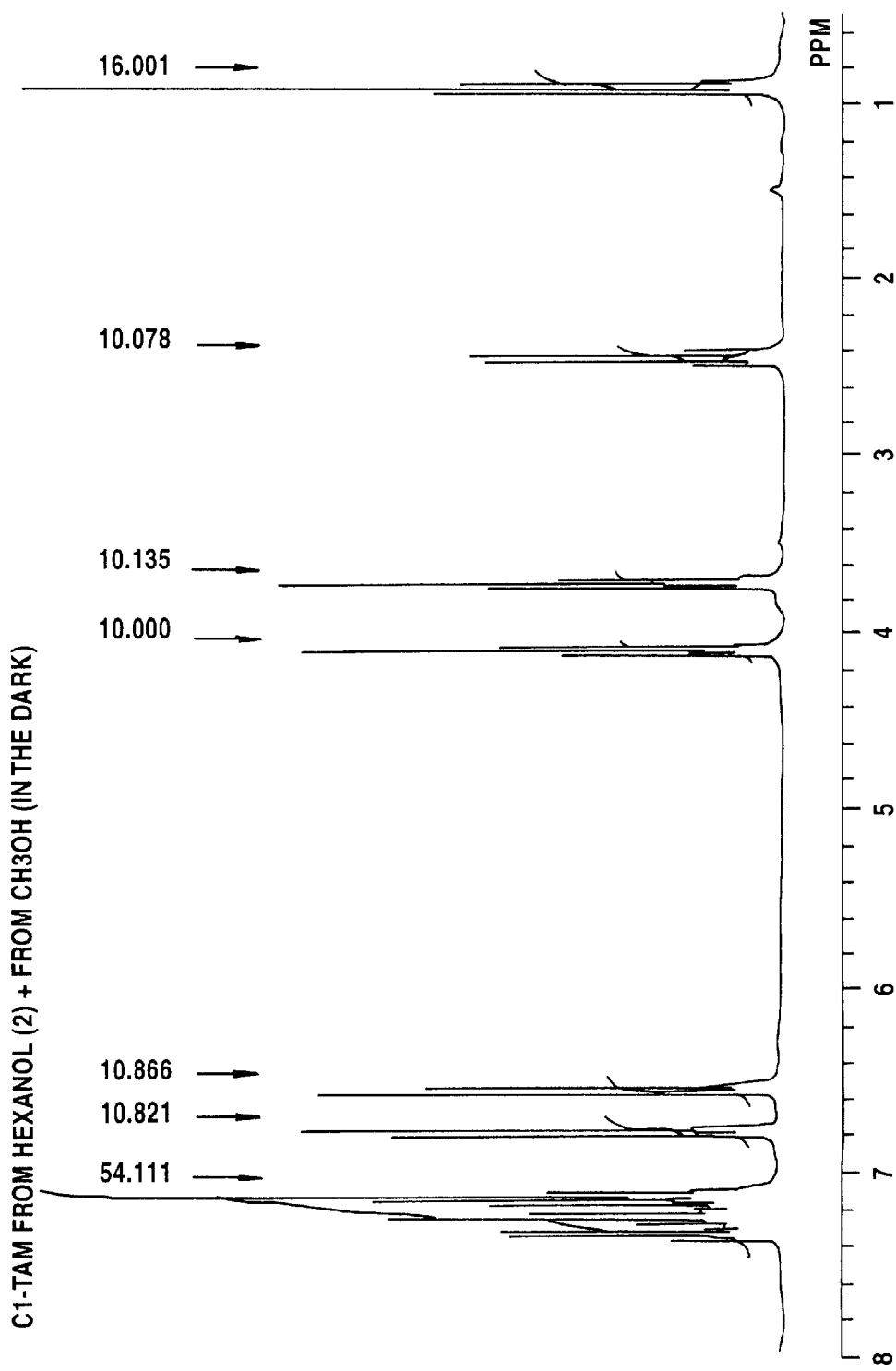
FIG. 7 is a $^1$H NMR spectrum of the material referred to in FIG. 5, after recrystallisation from methanol in the dark.
Figure 8:
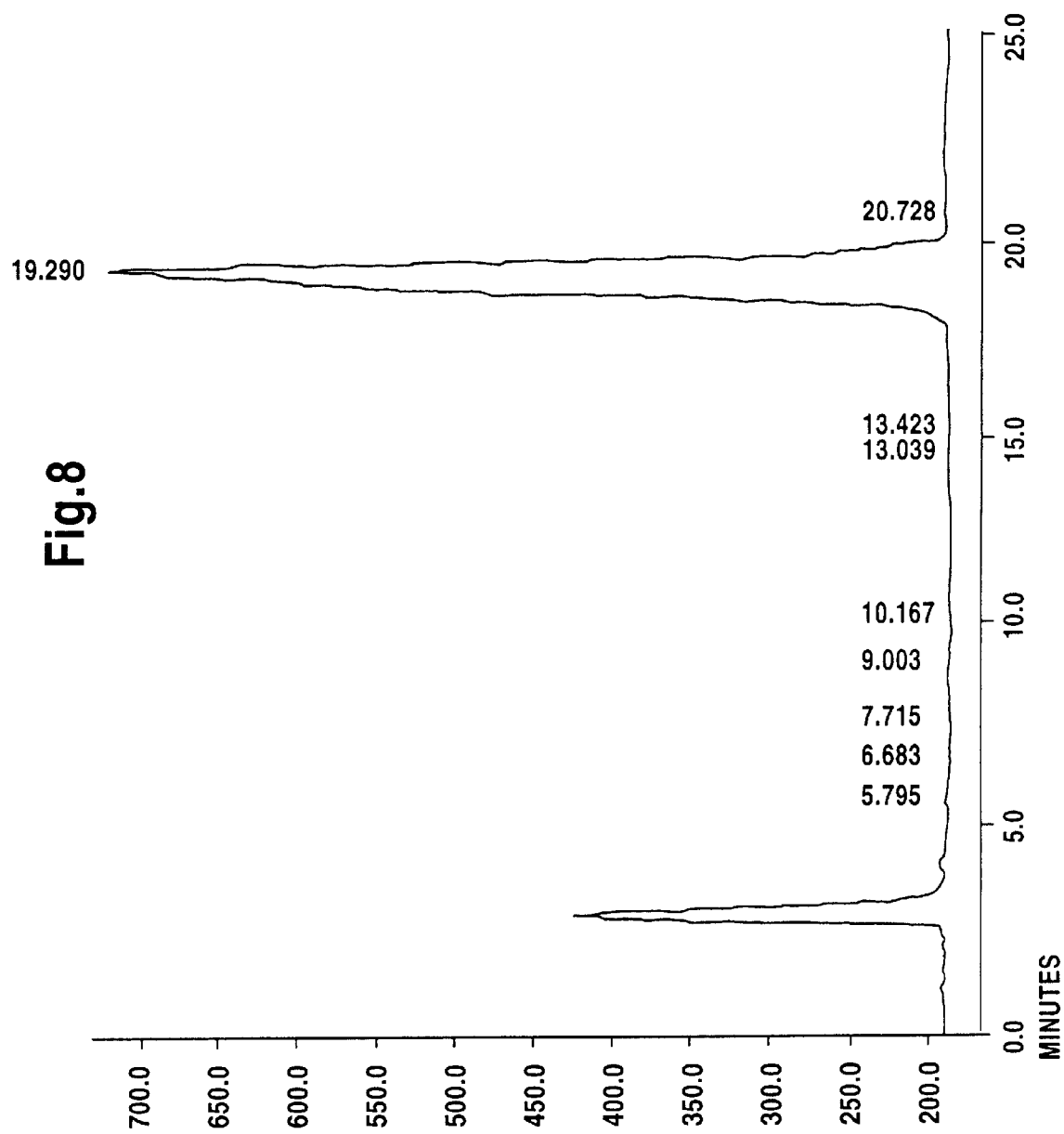
FIG. 8 is an HPLC analysis on the product of FIG. 7.

A solution of bromobenzene (3.92 g, 25 mmol) in ether (5 ml) containing a crystal of iodine was added dropwise to a suspension of magnesium turnings (0.63 g, 26 mmol) in ether (5 ml) at reflux. After the addition was complete, the reaction mixture was cooled to room temperature and a solution of 1-[4-(2-chloroethoxy)phenyl]-2-phenyl-1-butanone (3.75 g, 12.4 mmol) in ether (15 ml) was added over 1 hour. The resulting mixture was refluxed for 16 hours, then poured into dilute hydrochloric acid (50 ml) and extracted with ether (3×40 ml). The combined ether layers were concentrated, the residual oil was dissolved in ethanol (10 ml) and refluxed with concentrated hydrochloric acid (5 ml) for 4 hours. The organic phase was separated, dried (Na$_2$SO$_4$) and evaporated to dryness to give a yellow oil, which upon standing at room temperature for 5 minutes became a pale yellow solid (4.99 g, 111%—n.b. this yield suggests the presence of impurities). $^1$H NMR (see FIGS. 1 to 4 and discussion below) showed this to be a 2:1 mixture of the Z and E isomers. The solid was then covered with methanol and stirred at room temperature until a fine suspension formed. The suspension was filtered to give a pure white solid (3.82 g, 85%) which was a 3.2:1 mixture of Z:E isomers (see FIG. 5). The pure solid from above was dissolved in hot hexanol (100° C.) and left to crystallise at ambient temperature. A 22:1 mixture of Z:E isomers (2.11 g, 47% (see FIG. 6)) was produced, and this product was in turn recrystallised from methanol by dissolving the material in the minimum amount of boiling methanol to give pure (as confirmed by $^1$H NMR and HPLC—see FIGS. 7 and 8) Z isomer of 2-chloroethoxy tamoxifen (1.55 g, 34.6% yield). M.p. 107–109° C., m/z 362/364 (chlorine atom present). δ$_H$ 0.92 (3H, t, J=7.33 Hz, CH$_3$), 2.46 (2H, q, J=7.33 Hz, CH$_2$CH$_3$), 3.72 (2H, t, J=5.86 Hz, OCH$_2$CH$_2$Cl), 4.09 (2H, t, J=5.86 Hz, OCH$_2$CH$_2$Cl), 6.55 (2H, d, J=8.79 Hz, aromatic protons ortho to OCH$_2$CH$_2$Cl), 6.79 (2H, d, J=8.79 Hz, aromatic protons meta to OCH$_2$CH$_2$Cl), 7.10–7.38 (10H, m, the two remaining C$_6$H$_5$'s) (see FIG. 5). The 2-chloroethoxy tamoxifen was reacted with dimethylamine in ethanol, under reflux, to produce the desired Z isomer of tamoxifen.

Analysis of $^1$H NMR data

FIGS. 1 to 4 represent a mixture of the E- and Z-forms of compound XI described above in Scheme I.

The expansion of the region δ 0.80 to 1.05 shows two overlapping triplets corresponding to the $CH_3$ groups in the Z- and E-derivatives respectively. The critical point is the ratio of the heights of the peaks at 0.92 (for the Z) and 0.94 (for the E), which is approximately 2:1.

The expansion of the 4.00 to 4.35 region reveals similar information where ratios are 10:6.4 and 5.56:3.43. Similarly expansion of the region 3.6 to 3.9 shows the ratio to be 2.46:1. All of these measurements suggest an approximate 2:1 ratio. The discussion with reference to FIG. 1 also applies to the spectra of FIGS. 6 and 7 referred to below.

Figure 1:
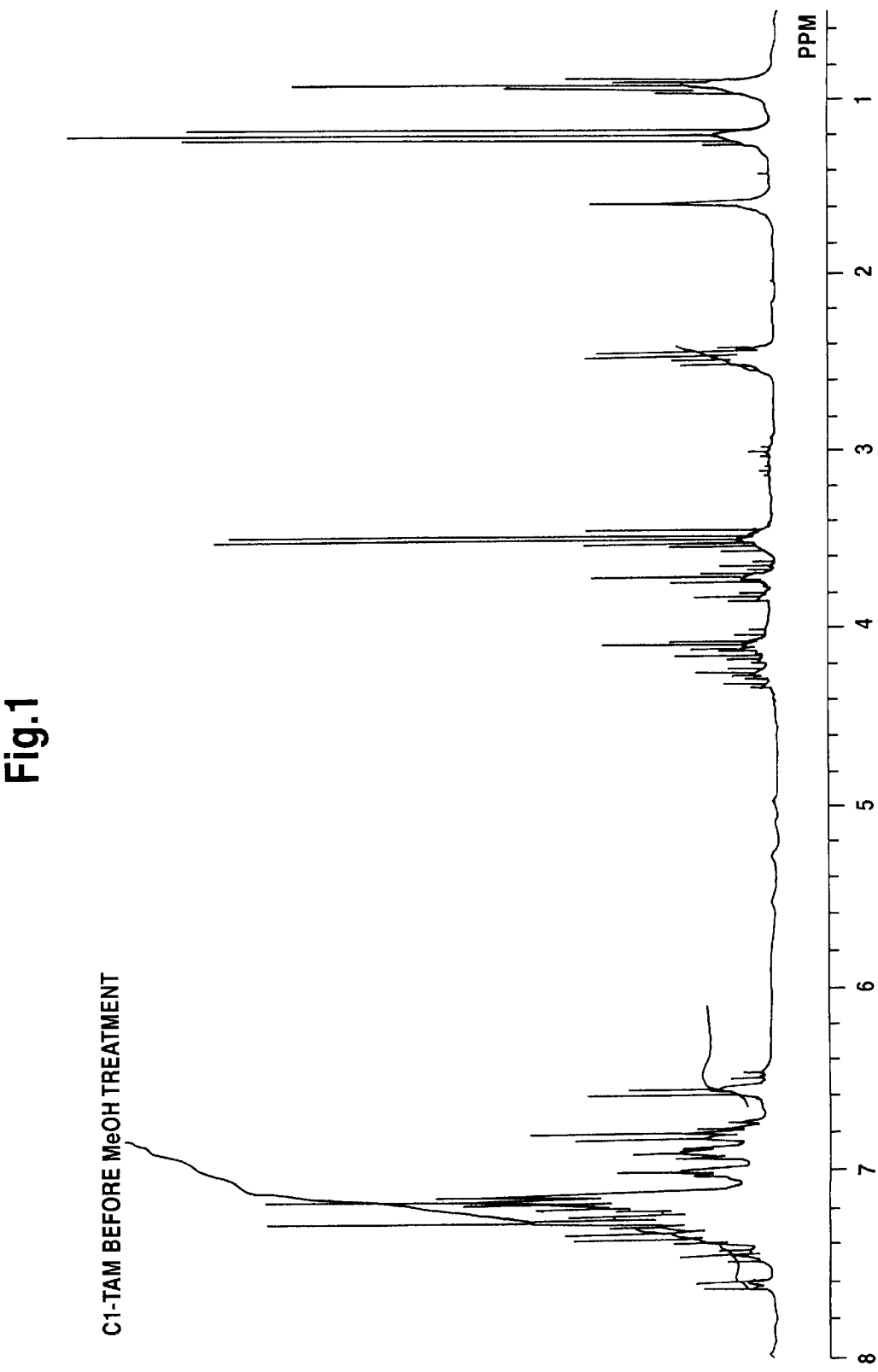
Figure 2:
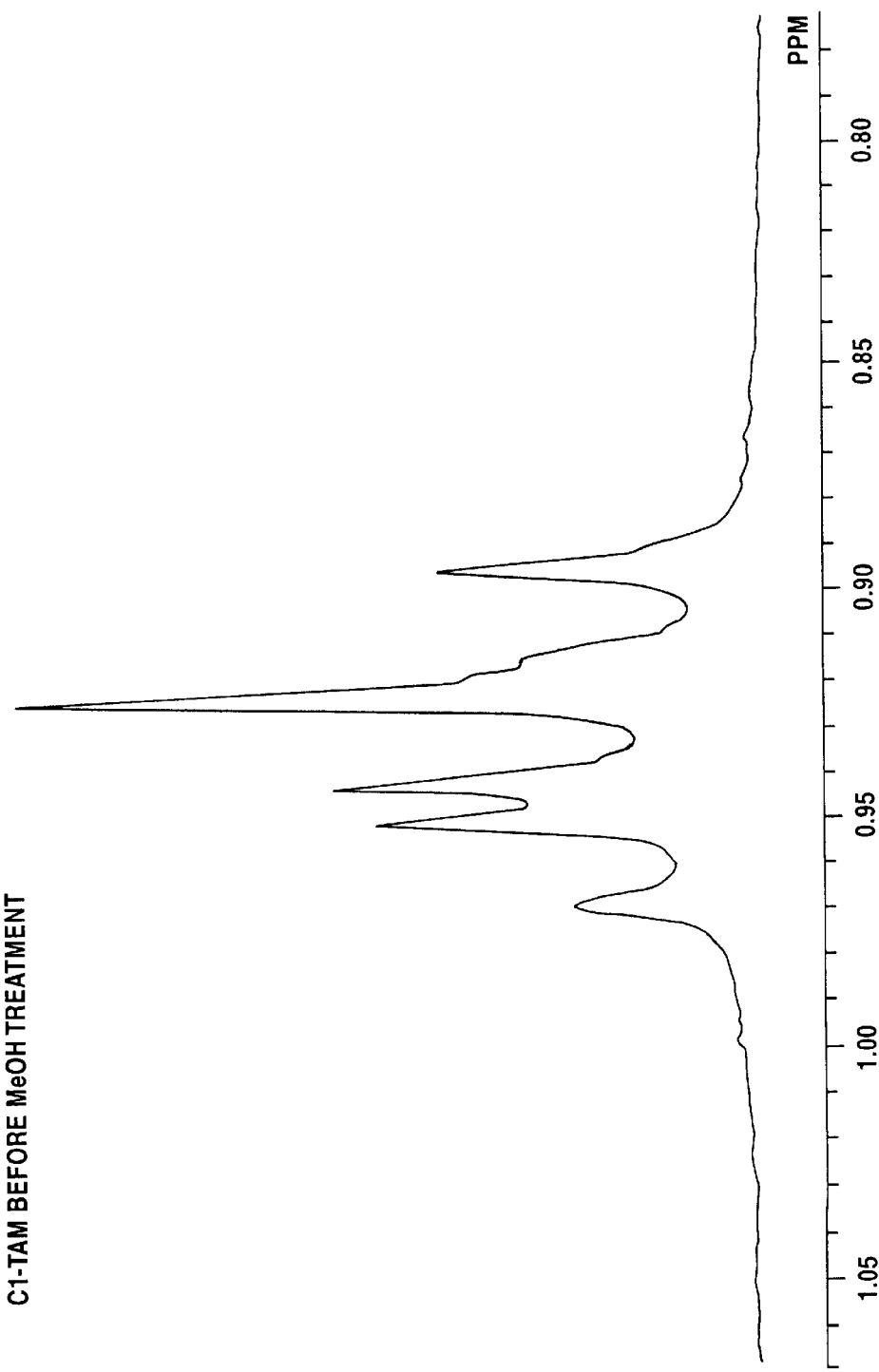
Figure 3:
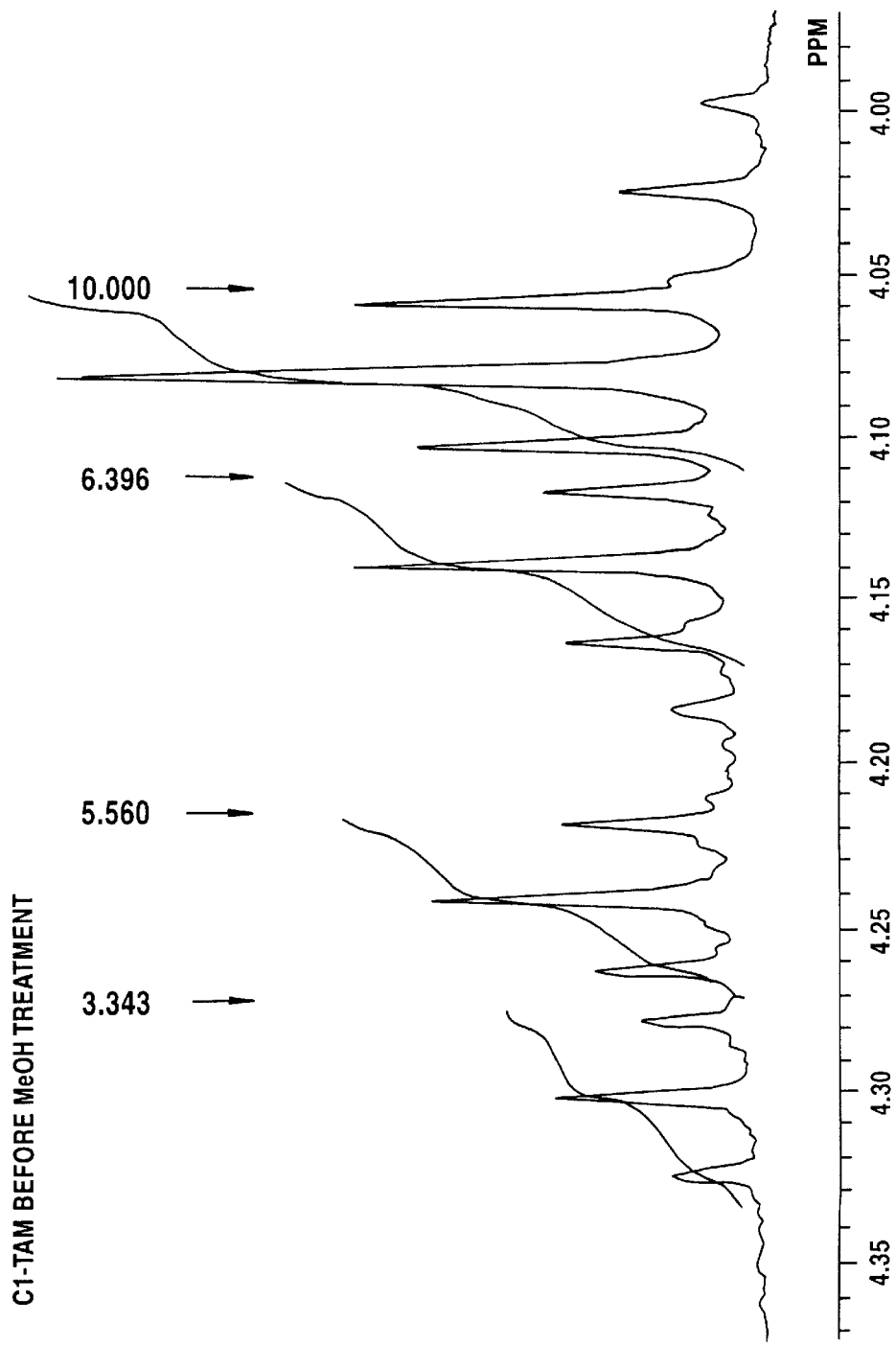
Figure 4:
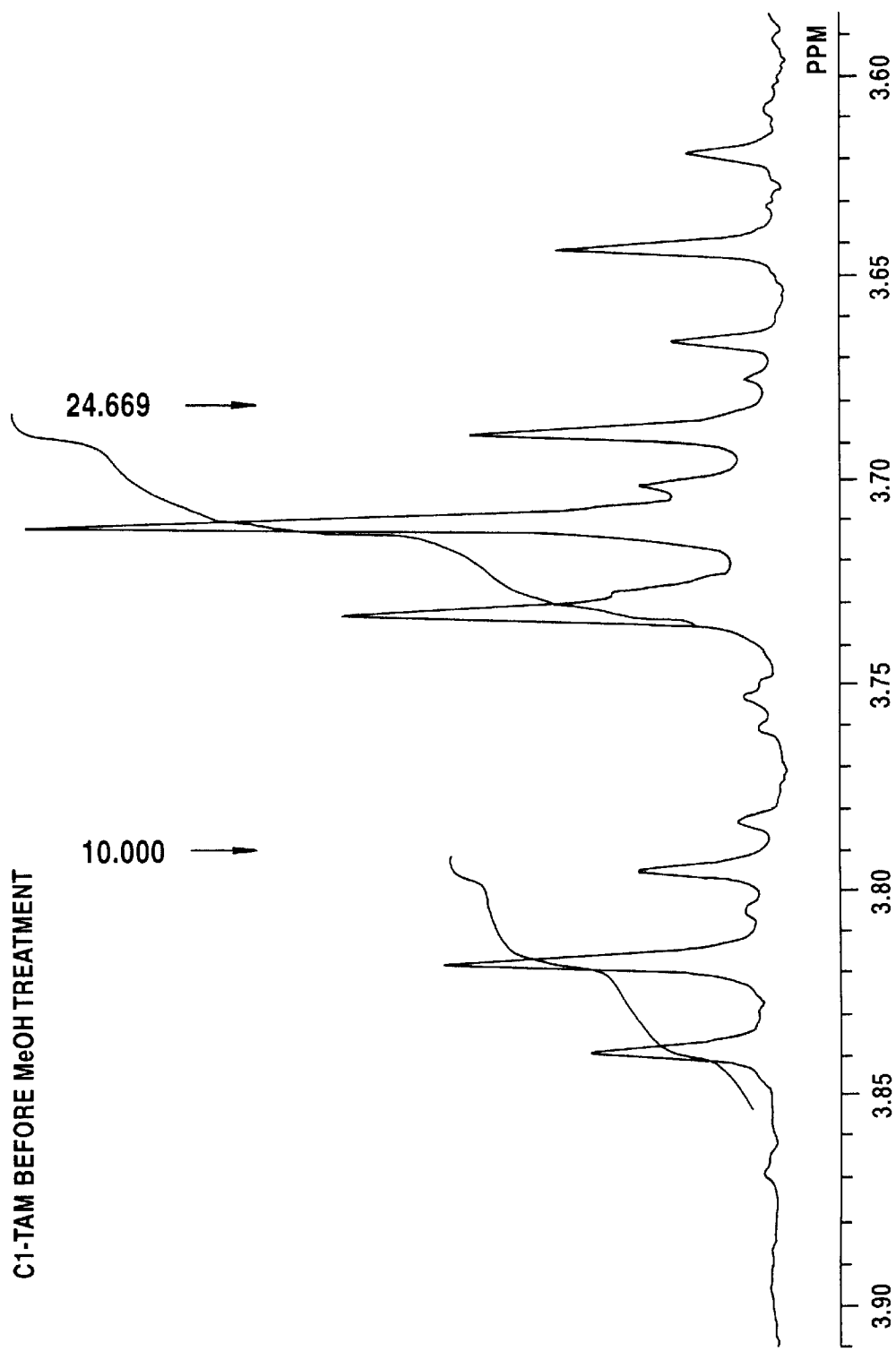
Figure 5:
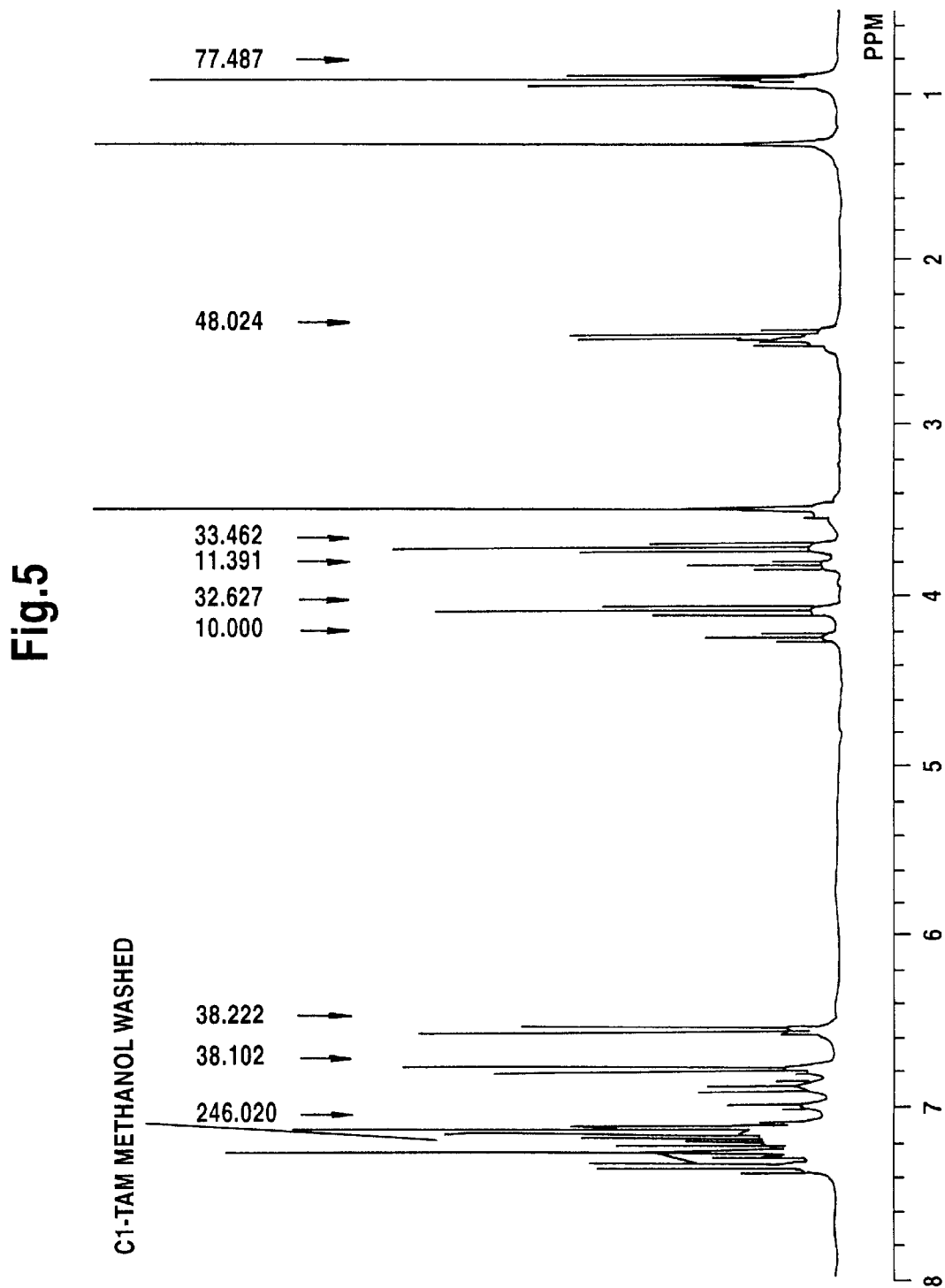
FIG. 5 is a $^1$H NMR spectrum for the product obtained in Example 1 after washing with methanol.
Figure 6:
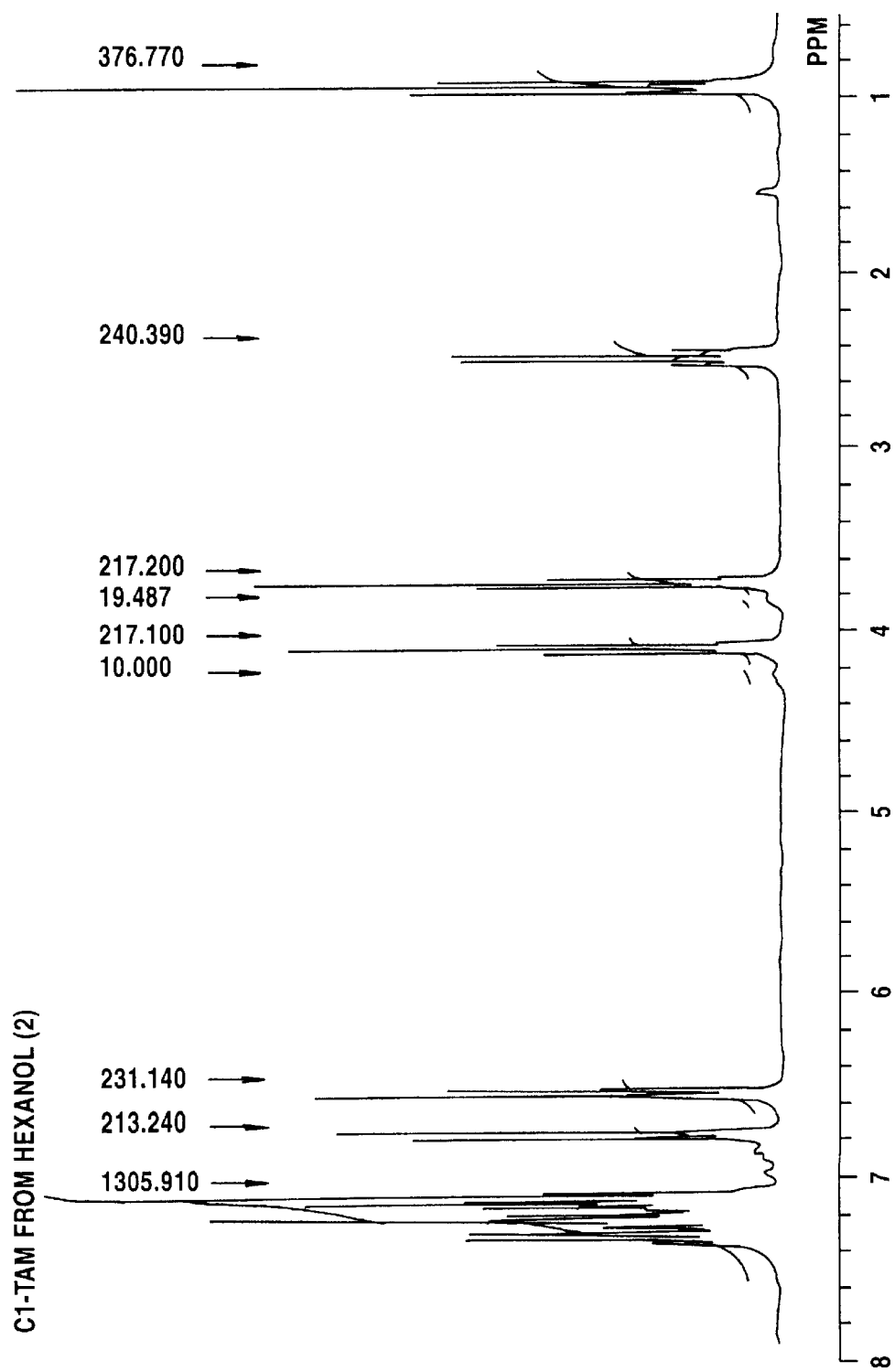
FIG. 6 is an $^1$H NMR spectrum of the material referred to in FIG. 5, after recrystallisation from hexanol in the dark.

FIG. 5 shows the $^1H$ NMR spectrum of the pure solid obtained after the methanol washing of the crude reaction product. FIG. 6 shows the $^1H$ NMR spectrum of the solid obtained following the recrystallisation from hexanol of the product shown in FIG. 5, and FIGS. 7 and 8 respectively show the $^1H$ NMR and the HPLC analyses of the pure Z isomer obtained following the second recrystallisation, this time from methanol. The HPLC analysis we carried out under the following conditions: Hypersil ODS 5 mm, 250× 4.0 mm column and 50% MeOH: 30%; MeCN: 20%; $H_2O$ mobile phase at 1 ml/min.

As an alternative to the use of hexanol followed by methanol as described in Example 1, other solvents were tested to assess their ability to predominantly remove the Z isomer of 2-chloroethoxy tamoxifen from a mixture of Z- and E-isomers. The following solvents were found to be effective: methanol, ethanol, propanol, iso-propanol, butanol, pentanol, cyclohexanol, acetonitrile, benzene, toluene, nitromethane, petroleum ether and dioxan.

EXAMPLE 2

Preparation of 4-Hydroxytamoxifen

A solution of 1,2-dibromoethane (1.41 g, 7.5 mmol) in ether (5 ml) was added dropwise with stirring to a boiling solution of 2,3,5,6-tetrafluoro-1-(4'-bromophenoxy)-4-(trifluoromethyl)benzene (3.89 g), 10 mmol) in ether (3 ml) containing magnesium turnings (486 mg, 20 mmol) under dried nitrogen in order to prepare a Grignard reagent. When the addition was complete, a solution of 1-[4-(2-chloroethoxy)phenyl]-2-phenyl-1-butanone (compound VIII) (3.02 g, 10 mmol) in ether was added. The resulting mixture was stirred at room temperature for 20 hours. The solution was then poured into dilute hydrochloric acid (75 ml) and extracted with ether (3×50 ml). The combined ether extracts were dried, concentrated, redissolved in absolute alcohol (10 ml) and refluxed with concentrated hydrochloric acid (3 ml) for 4 hours. The solution was then poured into water (25 ml) and extracted with ether (3×20 ml). The organic extracts were dried and concentrated to give a light brown oil (about 7 ml) which was dissolved in the same volume of methanol and left for 96 hours in a stoppered flask. Crystals of E isomer of compound X separated out of solution. M.p. 114–117° C. (lit. 116–118° C.), m/z 594, $\delta_H$ 0.92 (3H, t, J=7.51 Hz, $CH_3$), 2.45 (2H, q, J=7.51 Hz, $CH_2CH_3$), 3.73 (2H, t, J=5.86 Hz, $OCH_2CH_2Cl$), 4.10 (2H, t, J=5.86 Hz, $OCH_2CH_2Cl$), 6.57 (2H, d, J=8.8 Hz, aromatic protons ortho to $OCH_2CH_2Cl$), 6.77 (2H, d, J=8.8 Hz, aromatic protons meta to $OCH_2CH_2Cl$), 6.98 (2H, d, J=8.61 Hz, aromatic protons ortho to $OC_7F_7$), 7.09–7.18 (5H, m, $C_6H_5$), 7.22 (2H, d, J=8.61 Hz, aromatic protons meta to $OC_7F_7$). A typical yield for the E isomer starting from the ketone of formula VIII was 41%. The isolated E isomer of compound X can readily be converted to the desired oestrogenic isomer of 4-hydroxytamoxifen as described in, for example, J. Chem. Research, 1985 (S) 116, (M) 1342 and 1986 (S) 58, (M) 0771.

EXAMPLE 3

Preparation of Z isomer of 4-Hydroxytamoxifen

The procedure of Example 2 was followed except that the oil produced was dissolved in a 2:1 mixture of methanol and i-propanol. It was observed that a 41% yield of the desired E isomer was obtained in 4 hours.

EXAMPLE 4

Preparation of Z isomer of Tamoxifen

A solution of bromobenzene (3.92 g, 25 mmol) in ether (5 ml) containing a crystal of iodine was added dropwise to a suspension of magnesium turnings (0.63 g, 26 mmol) in ether (5 ml) at reflux, under nitrogen. After the addition was complete, the reaction mixture was cooled to room temperature and a solution of 1-[4-(2-chloroethoxy)phenyl]-2-phenyl-1-butanone (3.75 g, 12.4 mmol) in ether (15 ml) was added over 1 hour. The resulting mixture was refluxed for 16 hours, then poured into dilute hydrochloric acid (50 ml) and extracted with ether (3×40 ml). The combined ether layers were concentrated, the residual oil was dissolved in ethanol (10 ml) and refluxed with concentrated hydrochloric acid (5 ml) for 4 hours. The organic phase was separated, dried ($Na_2SO_4$) and evaporated to dryness to give a yellow oil. $^1H$ NMR showed this to be a 2:1 mixture of the Z and E isomers. The oil was then dissolved in warm methanol (about 40° C.) and allowed to cool to room temperature. The colourless crystals formed proved to be pure Z isomer of 2-chloroethoxy tamoxifen (4.12 g, 11.4 mmol, 92% yield). M.p. 107–109° C., m/z 362/364 (chlorine atom present), $\delta_H$ 0.92 (3H, t, J=7.33 Hz, $CH_3$), 2.46 (2H, q, J=7.33 Hz, $CH_2CH_3$), 3.72 (2H, t, J=5.86 Hz, $OCH_2CH_2Cl$), 4.09 (2H, t, J=5.86 Hz, $OCH_2CH_2Cl$), 6.55 (2H, d, J=8.79 Hz, aromatic protons ortho to $OCH_2CH_2Cl$), 6.79 (2H, d, J=8.79 Hz, aromatic protons meta to $OCH_2CH_2Cl$), 7.10–7.38 (10H, m, the two remaining $C_6H_5$'s). The 2-chloroethoxy tamoxifen was reacted with dimethylamine in ethanol, under reflux, to produce the desired Z isomer of tamoxifen.

What is claimed is:

1. A method of removing predominantly a first geometric isomer of a precursor of tamoxifen or a precursor of an analogue of tamoxifen from a mixture comprising said first geometric isomer and a second geometric isomer, wherein said first geometric isomer of said precursor is of formula

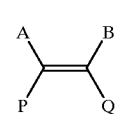

I wherein A represents a phenyl group substituted by a group-O—$(CH_2)_n$—X, where n is an integer and X is a leaving group; P represents an unsubstituted phenyl group; B represents an unsubstituted or mono-substituted phenyl group; and Q represents an optionally-substituted alkyl group, the method comprising contacting said mixture with a solvent which comprises methanol; and allowing the first geometric isomer to crystallize in said solvent.

2. The method according to claim 1, wherein said solvent is contacted with said mixture at a first temperature which is less than the boiling point of the solvent and recrystallization is then carried out at a second temperature which is greater than −4° C.

3. The method according to claim 2, wherein said second temperature is greater than 20° C.

4. The method according to claim 1, comprising allowing the first isomer to crystallize in a first solvent in a first step and subsequently allowing the crystallized product of the first step to crystalize in a second solvent in a second step, wherein said second solvent comprises methanol.

5. The method according to claim 4, wherein said second solvent has a lower boiling point than said first solvent.

6. The method according to claim 1, wherein the solvent comprises a mixture of solvents.

7. The method according to claim 1, wherein the solvent comprises a mixture of methanol and propanol.

8. The method according to claim 1, wherein n is in the range 1 to 8.

9. The method according to claim 1, wherein n represents 2.

10. The method according to claim 1, wherein X represents a chlorine atom.

11. The method according to claim 1, wherein B represents an unsubstituted phenyl group.

12. The method according to claim 1, wherein Q represents a $C_{1-2}$ alkyl group.

13. The method according to claim 1, wherein Q represents an unsubstituted alkyl group.

14. The method according to claim 1, wherein Q represents an ethyl group.

15. The method according to claim 1, wherein n represents 2, X represents a chlorine atom, B represents an unsubstituted phenyl group and Q represents an ethyl group.

16. The method according to claim 15, wherein said mixture is prepared from a compound of formula III

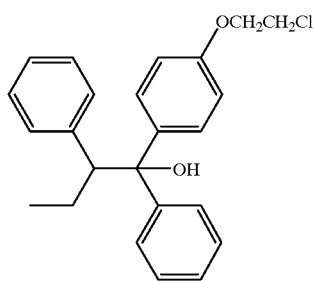

17. The method according to claim 16, wherein said compound of formula III is prepared from a compound of formula IV

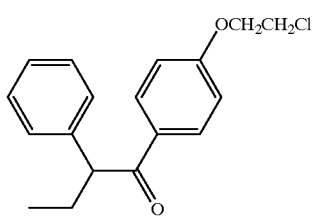

18. The method according to claim 17, wherein said compound of formula IV is prepared by treatment of a compound of formula

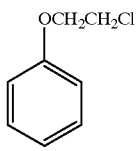

with a compound of formula

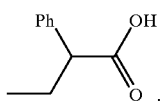

19. A method of preparing a compound of formula II

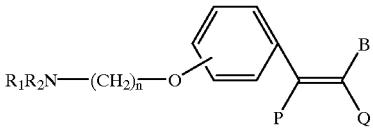

comprising derivatizing a first geometric isomer prepared as described in claim 1, wherein $R_1$ and $R_2$ independently represent a hydrogen atom or an unsubstituted or substituted alkyl group.

20. The method according to claim 19, wherein $R_1$ and $R_2$ represent methyl groups.

21. The method according to claim 19, wherein said compound of formula I is derivatized with dimethylamine to prepare the compound of formula II.

22. The method according to claim 4, wherein said first solvent comprises hexanol.

* * * * *